US00PP12630P2

(12) United States Plant Patent
Winchel

(10) Patent No.: US PP12,630 P2
(45) Date of Patent: May 21, 2002

(54) FLORIBUNDA ROSE PLANT NAMED 'WIN PTIG'

(75) Inventor: Joseph F. Winchel, Harbor City, CA (US)

(73) Assignee: Coiner Nursery, Laverne, CA (US)

( * ) Notice: Subject to any disclaimer, the term of this patent is extended or adjusted under 35 U.S.C. 154(b) by 0 days.

(21) Appl. No.: 09/483,454

(22) Filed: Jan. 12, 2000

(51) Int. Cl.[7] ..... A01H 5/00
(52) U.S. Cl. ..... Plt./143
(58) Field of Search ..... Plt./143

*Primary Examiner*—Bruce R. Campell
*Assistant Examiner*—Annette H. Para
(74) *Attorney, Agent, or Firm*—Christie, Parker & Hale, LLP

(57) ABSTRACT

A floribunda rose plant variety producing striped flowers.

1 Drawing Sheet

BACKGROUND OF THE INVENTION

The present invention relates to a new and distinct floribunda rose variety which was originated by my crossing as seed parent the variety known as 'Roller Coaster' and an undistributed, unnamed, unpatented seedling as pollen parent. The varietal denomination of this new rose is 'Win PTIG'. It is not known whether 'Roller Coaster' is patented.

SUMMARY OF THE INVENTION

Among the novel characteristics possessed by the new variety which distinguish it from its parents and all other varieties of which I am aware are its attractive striped flowers.

Asexual reproduction by budding of the new variety as performed in Watsonville, Calif, shows that the foregoing and other distinguishing characteristics come true to form and are established and transmitted through succeeding propagations. Other known forms of asexual reproduction may be also used.

COMPARISON WITH PARENT

The new variety distinguishes from its parent in flower size and color.

BRIEF DESCRIPTION OF ILLUSTRATION

The accompanying illustration shows typical specimens of the vegetative growth and flowers of the new variety in different stages of development and depicted in color as nearly true as it is reasonably possible to make the same in a color illustration of this character.

DESCRIPTION OF THE NEW VARIETY

The following is a detailed description of the new variety, from 2-year old specimens grown in Kern County, Calif., in the month of November. The color terminology used is in accordance with The Royal Horticultural Society Colour Chart (R.H.S.C.C.), and refers to plate numbers in the aforementioned color chart. Phenotypic expression may vary depending on light, environmental and cultural conditions.

FLOWER

Habit: Continuously.
Bud:
- *Size.*—About 1 inch long and ½ inch wide.
- *Form.*—Rounded.
- *Color.*—When sepals first divide near 66C.

Sepals: About ¾ inch, not as long as bud, near color 143C.
Peduncle:
- *Length.*—About ¼ inch.
- *Strength.*—Erect, sturdy.
- *Color.*—Near 143C.

BLOOM

Size: About 3½ inch diameter.
Borne: Usually in clusters of about 6 blooms.
Form: Flat, petals loosely rolled outward.
Petalage: About 27.
Color (⅓ to ½ open) outer petals: Top surface near 57A; under surface near 66A.
Inner petals: Top surface near 69C; under surface near 57A.
- *Base of petals.*—Near 69A.
- *General tonality from a distance.*—Variegated, striped mauve.

Color (fully open):
- *Outer petals.*—Top surface near 66A; underside near 66D.
- *Inner petals.*—Top surface near 65B; under surface near 69D.
- *Base of petals.*—Near 69D.
- *General tonality from a distance.*—Striped.

PETALS

About ⅛ inch long and about 1 inch wide.

Texture: Upperside semi-glossy, underside dull.
Appearance: Velvety.
Form: Oval.
Arrangement: Imbricated, regularly arranged.
Petaloids in center: None.
Persistence: Petals drop off cleanly.
Fragrance: Very strong old garden rose.
Lasting quality: Up to about 5 days on plant and after cutting.

REPRODUCTIVE ORGANS

Stamens, filaments and anthers:
*Arrangement.*—Regularly arranged.
*Color.*—Stamens: Near 11C. Anthers: Near 59A, about 87.
Pollen:
*Color.*—Near 23C.
Styles: Uneven, of different length color, color near 14B.
Hips: No hips observed.
Stigmas:
*Color.*—Near 11C.

PLANT

Form: Upright.
Growth: Very vigorous, height about 30 inches first season.
Foliage: Compound 5 leaflets.
*Size.*—About 2¼ inches long, about 1¼ inches wide, leaf, tip and apex pointed.
*Quantity.*—About 6 petal lengths.
*Color.*—New foliage: Upper side near 145B; underside near 145C. Old foliage: Upper side near 141A; underside near 143C.
*Shape.*—Oval.
*Texture.*—Upper side leathery, semi-glossy; underside leathery.
*Edge.*—Serrated.
*Serration.*—Slight.
*Disease resistance.*—Excellent resistance to mildew, blackspot and rust.
*Auricle.*—Short, pointed.
*Sepals.*—Upperside near 48C, underside near 143A, about 15/16 inch long, and about ¼ wide, smooth top and underside.
Wood:
*New shoots.*—Near 145A, smooth.
*Old wood.*—Near 145C.
Thorns:
*Quantity.*—About 14 per foot.
*Form.*—Curved downwardly.
*Length.*—Short.
*Color when young.*—77A.
*Position.*—Regular.
Prickles: None.
Flower stems from cut: About 2 to 5 inches.

WINTER HARDINESS

Completely winter hardy in Kern County, Calif.

I claim:

1. A new and distinct floridbunda rose plant of the variety substantially as shown and described.

* * * * *

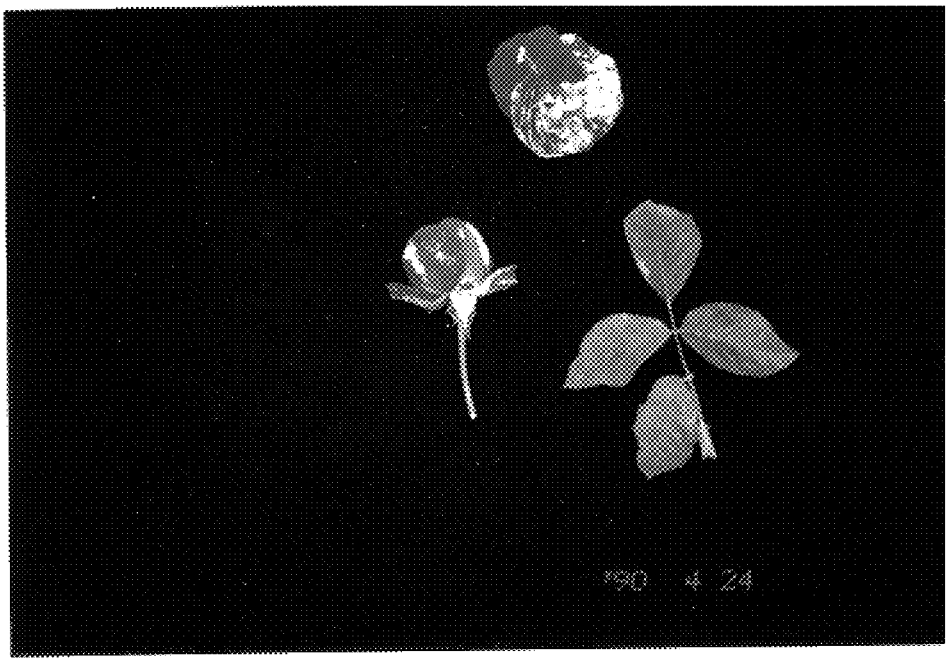
'90 4 24